United States Patent
Pesavento et al.

(10) Patent No.: US 6,520,913 B1
(45) Date of Patent: Feb. 18, 2003

(54) SYSTEM FOR RAPIDLY CALCULATING EXPANSION IMAGES FROM HIGH-FREQUENCY ULTRASONIC ECHO SIGNALS

(75) Inventors: Andreas Pesavento, Werl (DE); Helmut Ermert, Röttenbach (DE)

(73) Assignee: Lorenz & Pesavento Ingenieurbüro für Informationstechnik, Bochum (DE)

( * ) Notice: Subject to any disclaimer, the term of this patent is extended or adjusted under 35 U.S.C. 154(b) by 0 days.

(21) Appl. No.: 09/701,360
(22) PCT Filed: May 31, 1999
(86) PCT No.: PCT/EP99/03769
§ 371 (c)(1), (2), (4) Date: Nov. 28, 2000
(87) PCT Pub. No.: WO99/61903
PCT Pub. Date: Dec. 2, 1999

(30) Foreign Application Priority Data

May 29, 1998 (DE) .......................... 198 24 108

(51) Int. Cl.$^7$ .............................................. A61B 8/00
(52) U.S. Cl. ..................................... 600/438; 600/443
(58) Field of Search ............................. 600/437, 438, 600/443, 447, 587; 73/602, 599

(56) References Cited

U.S. PATENT DOCUMENTS

| | | | | |
|---|---|---|---|---|
| 5,235,983 A | * | 8/1993 | Iida et al. .................... | 600/443 |
| 5,309,914 A | * | 5/1994 | Iinuma ........................ | 600/443 |
| 5,383,462 A | * | 1/1995 | Hall ............................ | 600/455 |
| 5,495,771 A | * | 3/1996 | Sumi et al. .................... | 73/789 |
| 5,533,066 A | * | 7/1996 | Yamaguchi et al. ......... | 375/341 |
| 5,606,971 A | * | 3/1997 | Sarvazyan ................... | 600/438 |
| 5,669,386 A | * | 9/1997 | Thiele et al. ................ | 600/455 |
| 5,785,654 A | * | 7/1998 | Iinuma et al. ............... | 600/441 |
| 6,270,459 B1 | * | 8/2001 | Konafoglu et al. .......... | 600/449 |

* cited by examiner

Primary Examiner—Francis J. Jaworski
(74) Attorney, Agent, or Firm—Ursula B. Day

(57) ABSTRACT

Elastography is an ultrasound imaging method, which visualizes the elastic properties of biological tissue which is often impossible with conventional ultrasound images. The tissue is hereby compressed. The local tissue strain can be visualized by comparing the ultrasound images acquired before and after compression, in order to differentiate between hard and soft tissue types. In this comparison, the time shifts of corresponding ultrasound echo signals are computed locally at one or more locations, which is time-consuming with conventional methods.

The system for fast calculation of strain images from ultrasound echo signals described in this patent calculates iteratively the zero crossing of the phase of the complex HF-echo signals that are downshifted into the baseband. In this way, time shifts of corresponding echo signals can be computed quickly and accurately, so that values of the tissue strain can be determined, for example, in real time and displayed in parallel with the conventional ultrasound B-mode image.

9 Claims, 3 Drawing Sheets

SYSTEM FOR RAPIDLY CALCULATING EXPANSION IMAGES FROM HIGH-FREQUENCY ULTRASONIC ECHO SIGNALS

BACKGROUND OF THE INVENTION

The mechanical properties of biological tissue (e.g. parameters of elasticity) are of high interest for the characterization of the state of the tissue. In medical diagnostic, changes in the elastic properties reveal histological and possibly also pathological changes of tissue. Commonly known are the development of palpable swellings and lumps. In agriculture mechanical tissue properties are also of interest for the evaluation of the quality of meat.

PRIOR ART

Examination by palpation is inaccurate and insensitive. Elastography has a much better performance in this regard, because it technically measures the elastic tissue properties and visualizes them quantitatively or qualitatively in the form of cross sectional images [1]. In Elastography ultrasound is used, as it is used as an imaging method in medical diagnostics, but in a modified mode. In a series of sequential ultrasonic images even very small displacements and compressions inside the imaged tissue structures can be measured by the evaluation of the images sequences. A mechanical pressure to the tissue leads to a tissue compression and hence areas of different elastic properties will compress differently. The Elastography system will evaluate these compressions by a numerical comparison of the single images of the series. The strain is displayed in an image. The necessary compression of the tissue is applied externally by the transducer or internally by respiration or the heart beat. The compression is very small, usually some fractions of a millimeter in the order of 0.1%. A quantitative control of the pressure used for the compression is important. The pressure is applied in the propagation direction of the ultrasound.

A method for ultrasonic elastography on biological tissue was first described in 1991 by a paper of J. Ophir et al. [1], [2]. Ultrasound images, or more precisely the high-frequency ultrasound echo signals (HF-data) from which the ultrasound images are created in the ultrasound machine, are evaluated such, that the displacement of the tissue between two images under different tissue compression are calculated. Hence, conclusions about the elasticity can be drawn and even a quantitative reconstruction of the elastic modulus is possible.

The HF-echo signals of a compressed tissue area reach the transducer at a time, that depends on the degree of compression of the compressed tissue area. This causes differences in the propagation time of the echo signals due to the tissue compression, which leads to time shifts in corresponding segments of two echo signals that are acquired with a time delay under different compression of the tissue. Consequently, the main task of the evaluation of the HF-echoes (for the calculation of the strain) is the calculation of the time delay (=time shift) from short time intervals of the HF-echo signals. These time shifts between corresponding echo signals are calculated for at least two locations in the tissue or in the form of a two-dimensional image. For the calculation of time shifts the cross-correlation function of the HF-echo data is used. On one hand, the time shift can be found by maximizing the cross-correlation function [1]. On the other hand, the time shift can found using the phase of the correlation function, normally at zero lag [3,4].

After the calculation of the time shifts, the local strain can be computed by forming a gradient at at least one location in the tissue or also in the form of a two-dimensional image using simple linear filters [6] or by forming a difference, and optionally displayed.

All methods for the calculation of time shift use the cross-correlation function of corresponding intervals of the echo signals of the same tissue area under different compressions. The evaluation is time consuming because the integration has to be performed over the entire interval. The method proposed so far can be divided into two groups:

1) cross-correlation methods: methods, that determine the maximum of the cross-correlation function by a complete search or an iteration procedure. For this method the echo signals have to be sampled at a; very high sampling rates to be able to accurately calculate even very small time shifts. Hence, these methods are very time consuming and can not be implemented in real time or online-systems.

2) phase-based methods: methods, that estimate the time shift from the phase of a value of the cross-correlation function of the complex ultrasonic signals (analytic signals or baseband signals). The disadvantage of these methods are possible inaccuracies and the occurrence of ambiguities for large time shifts. Up to now, these ambiguities could only be prevented by additional, time consuming two dimensional pre or post-processing steps.

Due to the disadvantages of the conventional methods, it is not possible to process echo data with sufficiently accuracy to display strain images in real time. In the past it has been shown, that for ultrasonic imaging like the conventional b-mode or the Doppler sonography the real time capability is of fundamental importance for a wide acceptance of these systems. Another problem is, that the changes in the time-of-flight that result from the tissue compression depend on the distance between the tissue area and the transducer. That means, the time shift is not constant and increases monotonously with distance. The non-constant envelope of the echo signals leads to inaccuracies in the calculation of the time shifts, because for the calculation of the displacements an interval of finite length is used. In the past these inaccuracies have been reduced by a logarithmic amplitude compression of the actual HF-echo data [17]. A disadvantage of this techniques is that the phase of the signals change.

REFERENCES

[1] Ophir J., Céspedes I., Ponnekanti H., Yazdi Y., Li X.: "Elastography: A quantitative method for imaging the elasticity of biological tissues. *Ultrason. Imaging* 13, 111–114, 1991

[2] Céspedes I., Ophir J., Ponnekanti H., Maklad N.: Elastography: "Elasticity imaging using ultrasound with application to muscle and breast imaging in vivo." *Ultrason. Imaging* 15, 73–88, 1993

[3] O'Donnell M., Skovoroda A. R., Shapo B. M., Emilianov S. Y.: "Internal displacement and strain imaging using ultrasonic speckle tracking". *IEEE Trans. Ultrason., Ferroelect., Freq. Contr*, 41, 314–325, Mai 1994

[4] N. A. Cohn, S. Y. Emelianov, M. A. Lubinski, and M. A. O'Donnell, "An elasticity microscope. Part I: methods," *IEEE Trans. Ultrason., Ferroelect., Freq. Contr.*, vol. 44, pp. 1304–1319, 1997

[5] R. W. Schafer, und L. R. Rabiner, "A digital signal processing approach to interpolation," *Proc. of the IEEE*, vol. 61, pp. 692–702, 1973

[6] F. Kallel, und J. Ophir, "A least-squares strain estimator for elastography," *Ultrason. Imaging* 19, 195–208, 1997

[7] I. Céspedes, und J. Ophir, "Reduction of image noise in elastography," *Ultrason. Imaging*, vol. 15, pp. 89–102, 1993

SUMMARY OF THE INVENTION

The object of the invention is to develop a method and a system for processing ultrasonic echo data with sufficient speed and accuracy and/or computing precision (e.g. in real time) for determining values of the tissue distention. This method should yield the same accuracy as other cross-correlation methods using a computational efficient signal processing approach.

The object is solved by a method with the features of claim 1 and an apparatus with the features of claim 6. Phase based algorithms use the phase difference between two echo signals as a measure for the time shift. For single-frequency, time-shifted signals, the phase of the cross-correlation function of two complex echo signals (analytical signals) is a linear function of the time shift. At the actual time shift to be determined, the cross-correlation function has a root (zero crossing). The slope corresponds to the oscillation frequency of the single-frequency signal. This relationship can be exploited for calculating the time shift from a phase of the complex correlation function at an arbitrary position. However, due to the ambiguity of the arctan-function, the phase cannot be unambiguously calculated numerically. Furthermore, in pulse echo systems preferably broadband signals are used. For bandwidth-limited signals the above relationship between the time shift and the cross-correlation function is only approximately valid. This fact leads to the problems of inaccuracy and ambiguities of phase-based methods mentioned above.

Both problems (ambiguities and inaccuracies for broadband signals) can be solved by using iteratively the ultrasound phase of the cross-correlation function for the search of the maximum of the cross-correlation function, i.e. the zero crossing of the phase of the cross-correlation function. The echo data acquired by the transducer are arranged in A-lines according to FIG. 1. The calculation of the time shift is done at different discrete locations in the tissue or at least at one location in the tissue. In elastography the time shift as a function of depth at these discrete points is a monotone function. For each A-line the time shifts are successively calculated beginning with the point closest to the ultrasound transducer and continuing to the deepest point. At the point closest to the ultrasound transducer, the phase of the value of.the cross-correlation function in unique in spite of the ambiguity of the arctan-function, since the time shifts are very small. For the calculation of the time shift at one point or depth, respectively, the following iteration is performed:

1) The iteration starts at the estimated time shift $\tau$, that has been calculated at the point in the same A-line closer to the transducer. For calculating the points closest to the ultrasound transducer, the iteration starts at zero.

2) The phase of the cross-correlation function of the corresponding ultrasonic echo data at the estimated time shift r is calculated (within a $-\pi$ and $+\pi$ band).

Due to the above explanations, the calculated phase is approximately proportional to the distance of the estimated shift $\tau$ to the real time shift. The proportionality factor approximately corresponds to the centroid frequency of the ultrasound transducer. Consequently, the estimation of the time shift X can be improved by converting the remaining phase to a time shift through division by the centroid frequency and changing the present estimate of the time shift accordingly.

Process step 1) assures that the correlation function is always evaluated in the vicinity of the true time shift. And hence, the remaining phase shift can be determined unambiguously in spite of the ambiguity in the arctan-function and converted to a time shift. By a repeated iteration of 2) inaccuracies of the conversion from phase shifts to time shifts for the use of broadband signals can be iteratively minimized.

With this method, the cross-correlation function has to calculated only a few times (less than 10 times) to obtain a sufficiently accurate estimate of a time shift. Hence, the proposed method is iterative in two ways: time shifts are calculated by an iterative use of the calculated time shifts of the same or preceding image points.

Since in elastography very small time shifts have to be estimated, which are frequently smaller than the sampling time, the echo signals have to be suitably interpolated. The proposed method uses, like [3] and [4], complex baseband-shifted signals for the calculation of the cross-correlation function. The echo signals are shifted to the baseband immediately after the echo signals are recorded. Since these have, due to the bandpass limitation of ultrasound echo signals a significantly reduced upper frequency, a computationally efficient linear interpolation between values of the echo signals is sufficient to also compute values of the cross-correlation function of corresponding echo signals with time shifts that are not integer multiples of the scan time Inaccuracies in the estimated time shifts can be reduced by this method by using a logarithmic amplitude compression of the complex baseband signals, after these have been incremented by one. Using this method the phase of the base band signals remain unchanged. Consequently the logarithmic compression can also be used for phase based methods.

Unlike currently used phase-based methods, the proposed method reaches the same accuracy as the cross-correlation method. Furthermore the cross-correlation function only has to be evaluated a few times (less than 10 times) to accurately calculating the time shift. Consequently, real time processing of the echo signals for the calculation of tissue strains is already possible by using a suitable signal processing unit which is available in modern ultrasonic machines or are otherwise commercially available or can be fabricated in form of digital circuits.

DETAILED DESCRIPTION OF PREFERRED EMBODIMENTS

Figure 2:
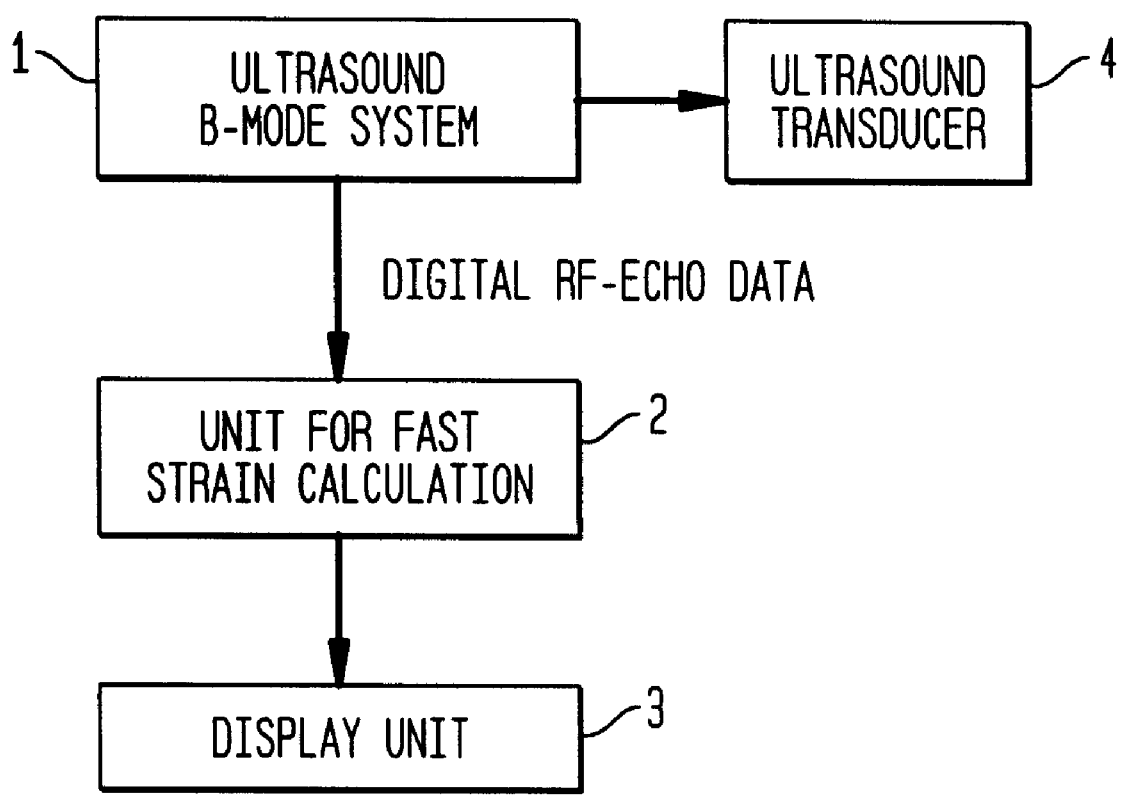
FIG. 2: Schematic diagram of the entire system of a preferred embodiment. The system includes a conventional ultrasound B-mode system (5) with one or more transducers (1). The strain images (10) are calculated by a computer unit (6) and displayed on a display.

Certain embodiments of the invention are illustrated in the drawings and will be described in detail below:
Schematic Diagram of a System for the Acquisition, Fast Calculation and Display of Strain Images (FIG. 2)

Figure 3:
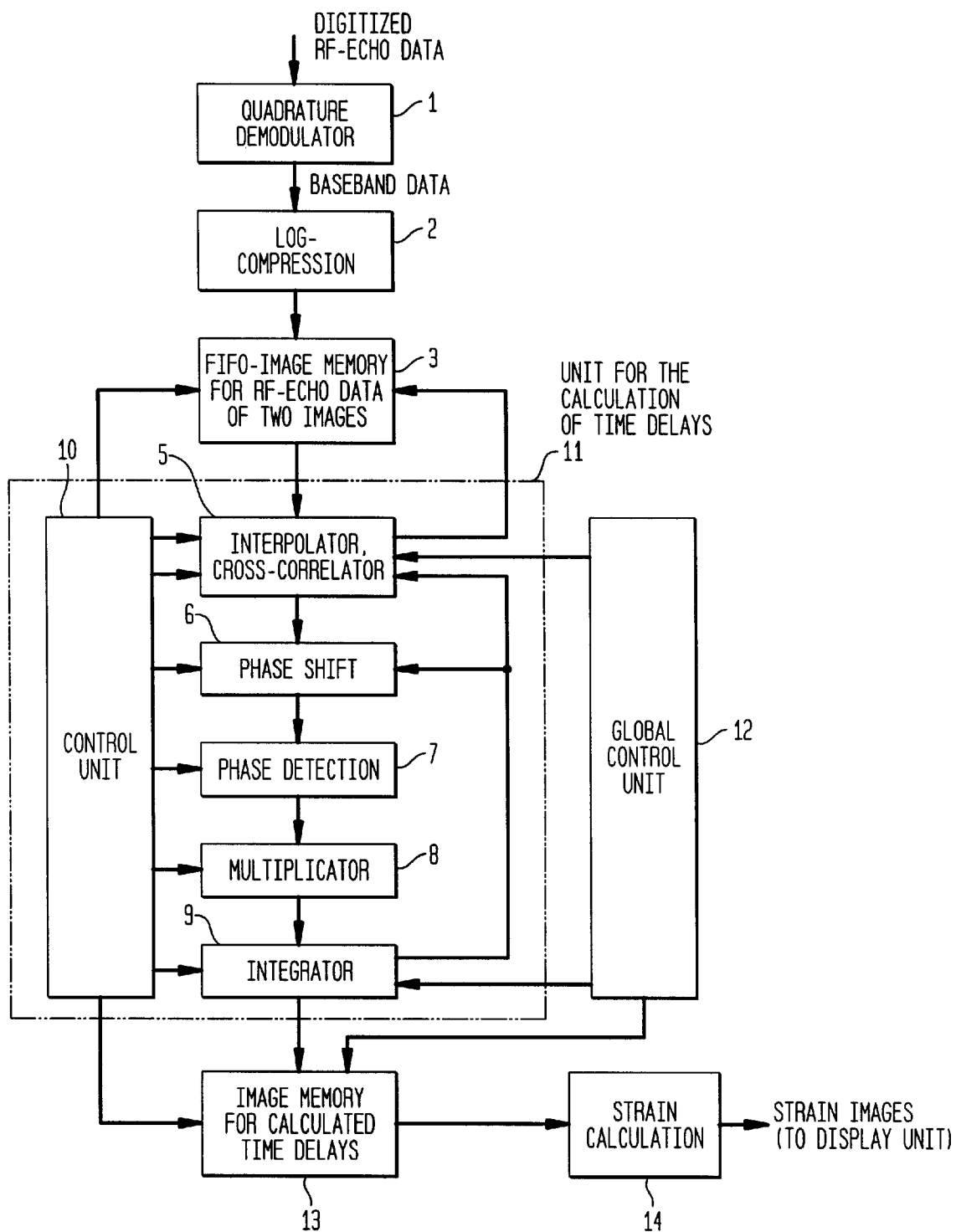
FIG. 3: Embodiment of a computer unit (6), where the strain is calculated by an iterative analysis of the phases of the cross-correlation function of at least two echo signals. The echo signals are recorded with a transducer (4) connected to an ultrasound B-mode system (1). The computer unit (2) (6) calculates strain images (10) from the HF-echo data applied to the input and acquired with the B-mode system (5). The strain images are transferred to the display (4) (7). Before the calculation of the strain, the echo data are transformed into baseband signals (14) by a quadrature demodulator (11). The calculation of the time delays is done in the time delay estimation unit (21).

The system for the acquisition, fast calculation and display of strain images includes three functional units:

a) a conventional ultrasound machine (1), (5) with one or more ultrasound transducers (4), (1). These transducers can acquire ultrasonic echo data with different scan modes (sector scan, parallel scan). Furthermore the kind of focusing (electronic focussing or single-element transducer with constant focus) is of no importance. The HF-echo data have to be available in digital format. For systems with analog beamformer or of for systems with a single element transducer, the HF-echoes have to be acquired and digitized directly after the beam-former or the single element transducer. For systems with digital beamformer the digital HF-echoes can be accessed directly.

b) a computer unit (2), (6) for fast calculation of strains. This is the core of the invention. This computer unit can reside inside or outside of the ultrasonic machine. The computer unit can be implemented by a digital circuit, by a DSP-board, an external computer, or a computer unit of the ultrasound machine (see FIG. 3).

c) a display unit (3), (7): This display unit can reside inside or outside the ultrasound machine, too. The visualization capabilities of an ultrasound machine can also be used. When the system is linked to an external computer, the graphic capabilities of this computer can be used.

The calculation of the strain images can be performed in real time, on-line of offline after the acquisition of ultrasonic echo data. For the depiction of strain images, the strain image can be displayed completely, a part of the B-mode image can be replaced by the strain image in a specific area (region of interest), or the B-mode image could be represented by a gray scale or color scale.
Implementation of the computational unit (FIG. 2, 3)

The computer unit can be implemented in the following manner, for example as a digital circuit: first the HF-echo data have to be quadrature demodulated (11). The resulting data (14) are shifted to the baseband and have a complex value, referred to as baseband data or IQ-data. The amplitude of the baseband-data is now optionally logarithmically compressed (12).

The processed baseband data are stored in an intermediate memory (13). This intermediate memory has to be able to store the baseband data (14) of two consecutive temporal B-mode images. However, at least the baseband data of two echo signals that are recorded under different tissue compression with a time offset have to be stored.

According to the FIFO-principle, the memory can delete always delete the echo data of the last but one image, if baseband data of a new image are supplied to the input.

Figure 1:
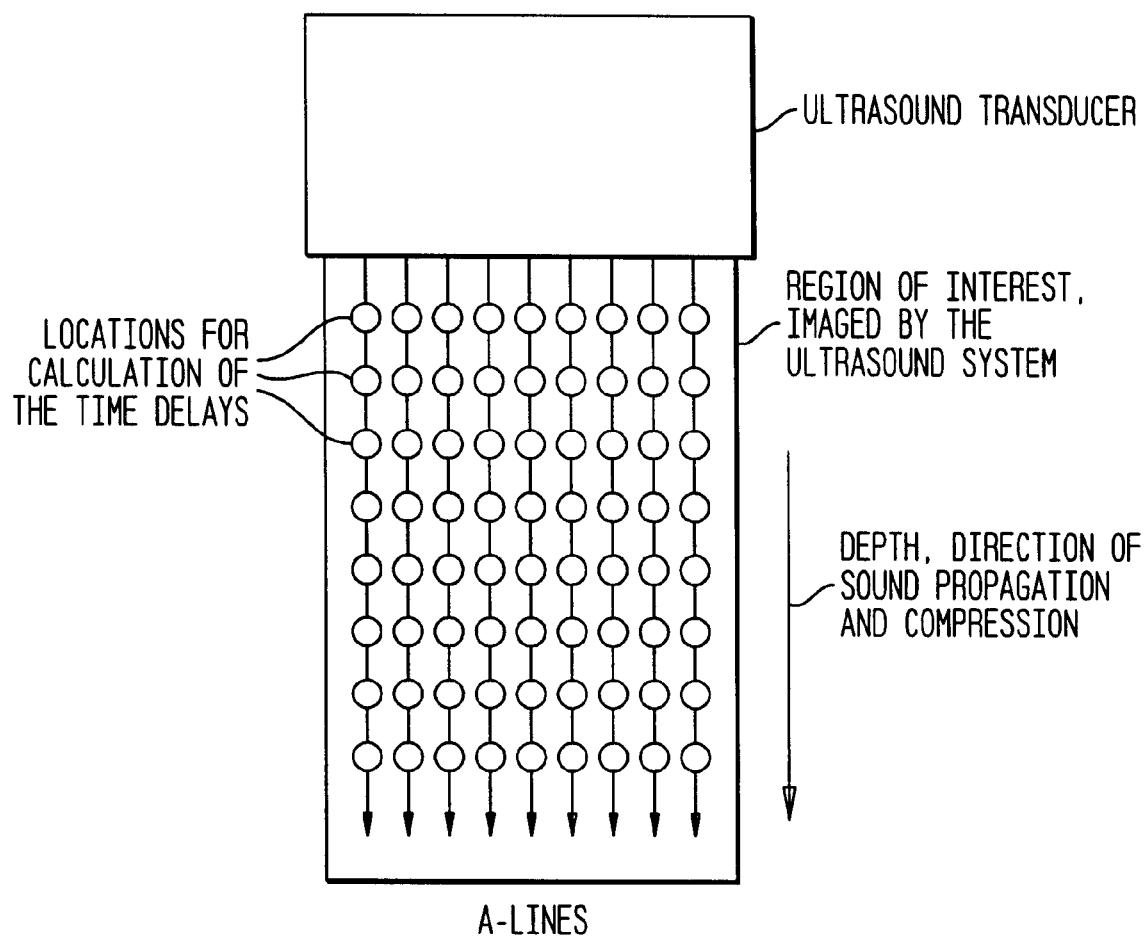
FIG. 1: Possible setup of ultrasound echo signals (3) and also time delay estimation and strain images. The ultrasound echo signals, which are received by the transducer (1), are organized in A-lines(3). At each discrete point (4) a time shift can be calculated between the echo of the compressed and uncompressed tissue. From these time shifts the strain is computed at the same discrete positions which form a two-dimensional image of the strain. The calculation of the time delays for each A-line starts with the point located closest to the transducer.

The calculation of time shifts is done in a separate unit (11), (21), which may exist several times in a digital circuitry. Hence the time shifts of several A-lines can be calculated at the same time. The sequence is controlled by the global process control unit (12), (22). This process control unit controls the calculation of time shifts at different discrete positions (2). According to FIG. 1, the time shifts are computed for one or different discrete pixels. Different A-lines can be processed parallel or sequentially. The calculation of time shifts of an A-line starts with the points closest to the transducer, then calculating successively time shifts at deeper points. The process has to be controlled by the global process control unit (12), (22).

The unit for calculating a time shift (11), (21) includes the following elements: Values of the complex cross-correlation function of the two echo signals are evaluated by an integrator (19) at a predetermined position (15). The integrator (19) serves as a memory for the estimated time shift τ during the iteration. Its starting value has to be set by the global process control unit. The starting value for the pixel closest to the transducer is zero. The starting value for all other pixels is the time shift calculated for the point that is closer to the transducer. The position of the interval of the corresponding echo signals that is used for calculating the cross-correlation function is determined by the global process control unit (12), (22). It is an interval of constant length surrounding the point, for which the time shift is to be calculated. In order to be able to calculate the cross-correlation function also at those positions, which are not integer multiples of the sampling time, the data are linearly interpolated by an interpolator (15). It accesses the baseband echo data of the same A-lines of both B-mode images in the image memory using different compression. Consequently, a value of the cross-correlation function of the baseband data is calculated in (15). In order to obtain the cross-correlation function of the complex HF-echo data at this time shift, the phase of the result has to be rotated in a negative direction (6), (19, 16) by the product of the oscillation frequency of the mixer (11) with the time delay at which the cross-correlation function is evaluated (9). The phase of the resulting complex number is now calculated (17) and multiplied (18) by the reciprocal value of the centroid frequency of the transducer (oscillation frequency) to convert the phase value into a time shift. The result is added to the value of the interpolator (19). The process between (5) and (9), (15) and (19) has to be repeated several times (between 1–10 times). This is controlled by the process control unit (10),(20). The result of the iteration is the desired time shift which is stored in an image memory (13), (23). The location at which the result is stored is determined by the global process control unit. The content of the image memory can then be displayed after converting the time shift data with a filter (14),(24) to the desired strain data.

All elements of the computer unit can be implemented technically in several different ways:

1. Each element or several elements can be implemented by a digital logical circuit 2. Each element or several elements can be implemented by one or several DSP units or microprocessors.

3. Each element or several elements can be implemented by a computer located inside or outside of the ultrasound machine.

What is claimed is:

1. A method for the determination of strain in human and animal elastic tissue using ultrasound comprising the following steps:

recording at least two echo signals at different times by means of an ultrasound transducer;

determining an estimated time delay between at least two recorded echo signals using a cross correlation function of the at least two recorded echo signals; said time delay being determined by an iterative evaluation of the complex phase of the cross-correlation function;

determining at least one strain value from two estimated time delays so determined.

2. The method of claim 1, wherein the iterative evaluation of phases in transducer proximate sections of tissue is carried out using the time delays as starting points for an integrative search in sections further away from the transducer.

3. The method of claim 1, wherein the strain values are displayed in a two-dimensional image.

4. The method of claim 1, further comprising the steps of frequency shifting the ultrasound data by mixing the data into a baseband; and conducting linear interpolation between two values of the at least two mixed echo signals.

5. The method of claim 4, wherein the mixed echo signals have phase amplitudes which are logarithmically compressed under retention of the phase.

6. An apparatus for measuring the strain of human and animal elastic tissue using ultrasound comprising:

a transducer (1) for recording at least two echo signals at different times;

a device for determining at least one time delay (21) by iterative evaluation of the phases of a plurality of complex values obtained by a cross correlation function of the at least two echo signals a device for computing the strain from at least one time delay.

7. The apparatus of claim 6, further comprising a unit for displaying a two dimensional image representing a number of strain values and comprising values of gray or values coded for color.

8. The apparatus of claim 6, further comprising a unit for frequence shifting and mixing the echo signals and a unit for carrying out linear interpolation between values of the at least two mixed echo signals.

9. The apparatus of claim 6, further comprising a device for the carrying out logarithmic compression of amplitudes of the mixed echo signals.

* * * * *

UNITED STATES PATENT AND TRADEMARK OFFICE
CERTIFICATE OF CORRECTION

PATENT NO. : 6,520,913 B1
DATED : February 18, 2003
INVENTOR(S) : Andreas Pesavento and Helmut Ermert It is certified that error appears in the above-identified patent and that said Letters Patent is hereby corrected as shown below:

Column 1,
Line 64, after ".. shift can .." insert -- be --

Column 2,
Line 13, after "… sampled at …" delete "a;"
Line 27, replace "… sufficiently …" with -- sufficient --
Line 42, replace "… techniques…" with -- technique --

Column 3,
Line 47, after "..function .." replace "in" with -- is --

Column 4,
Line 9, after "..has to.." insert -- be --
Line 33, replace "… remain …" with -- remains --

Column 5,
Line 23, after "..or .." delete "of"
Line 43, replace first "… of …" with -- or --
Line 63, delete "delete"

Signed and Sealed this

Twenty-ninth Day of July, 2003

JAMES E. ROGAN
*Director of the United States Patent and Trademark Office*